United States Patent [19]

Harman et al.

[11] Patent Number: 5,742,718

[45] Date of Patent: Apr. 21, 1998

[54] PROPRIETARY FIBER CONNECTOR AND ELECTRONIC SECURITY SYSTEM

[75] Inventors: Stuart D. Harman, San Jose; Mark Roush, Los Gatos, both of Calif.

[73] Assignee: Eclipse Surgical Technologies, Inc., Sunnyvale, Calif.

[21] Appl. No.: 696,301

[22] Filed: Aug. 13, 1996

[51] Int. Cl.$^6$ .................................................. G02B 6/36
[52] U.S. Cl. .............................. 385/53; 385/88; D24/107
[58] Field of Search ................................ 385/53, 88, 92

[56] References Cited

U.S. PATENT DOCUMENTS

| | | | |
|---|---|---|---|
| 4,258,977 | 3/1981 | Lukas et al. | 385/65 |
| 4,519,390 | 5/1985 | Horne. | |
| 4,766,433 | 8/1988 | Herman et al. | 340/825.31 |
| 4,919,508 | 4/1990 | Grace et al.. | |
| 4,998,794 | 3/1991 | Holzman. | |
| 5,016,964 | 5/1991 | Donnelly. | |
| 5,134,469 | 7/1992 | Uchimura | 358/98 |
| 5,142,598 | 8/1992 | Tabone | 385/78 |
| 5,521,392 | 5/1996 | Kennedy et al. | 250/492.1 |
| 5,623,357 | 4/1997 | Kight et al. | 359/135 |

*Primary Examiner*—John D. Lee
*Assistant Examiner*—Ellen E. Kang
*Attorney, Agent, or Firm*—Janet Kaiser Castaneda

[57] ABSTRACT

A laser connector and electronic security system for a laser delivery system controls connection of the delivery system to a source of laser energy for medical procedures by storing encrypting codes to allow access by authorized, unused, delivery assemblies. The connector is specially dimensioned to further control delivery system access to the source, and the electronic security system utilizes EEPROM memory to allow storage and accumulation of information about the laser parameters used in the medical procedure. The connector and electronic security system is particularly suitable for pulsed laser transmyocardial revascularization (TMR) procedures and enables automatic power level calibration in accordance with the connected delivery system specifications, maximum time of usage settings, storage of the number/power level of the pulses delivered, and storage of the total number of TMR channels created.

24 Claims, 9 Drawing Sheets

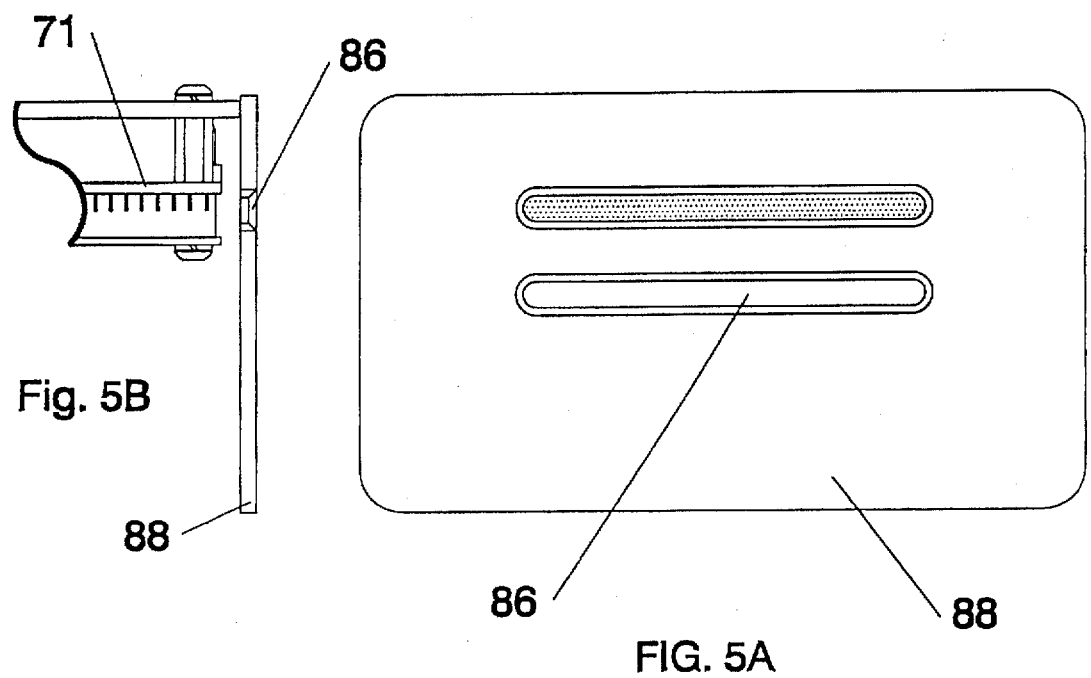
Fig. 5B
FIG. 5A
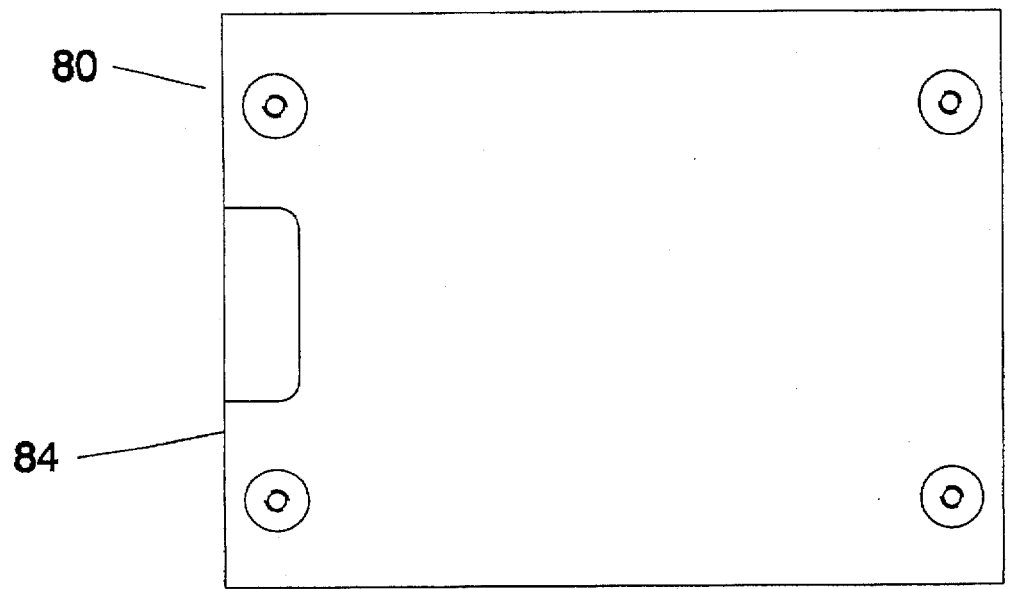
Fig. 6

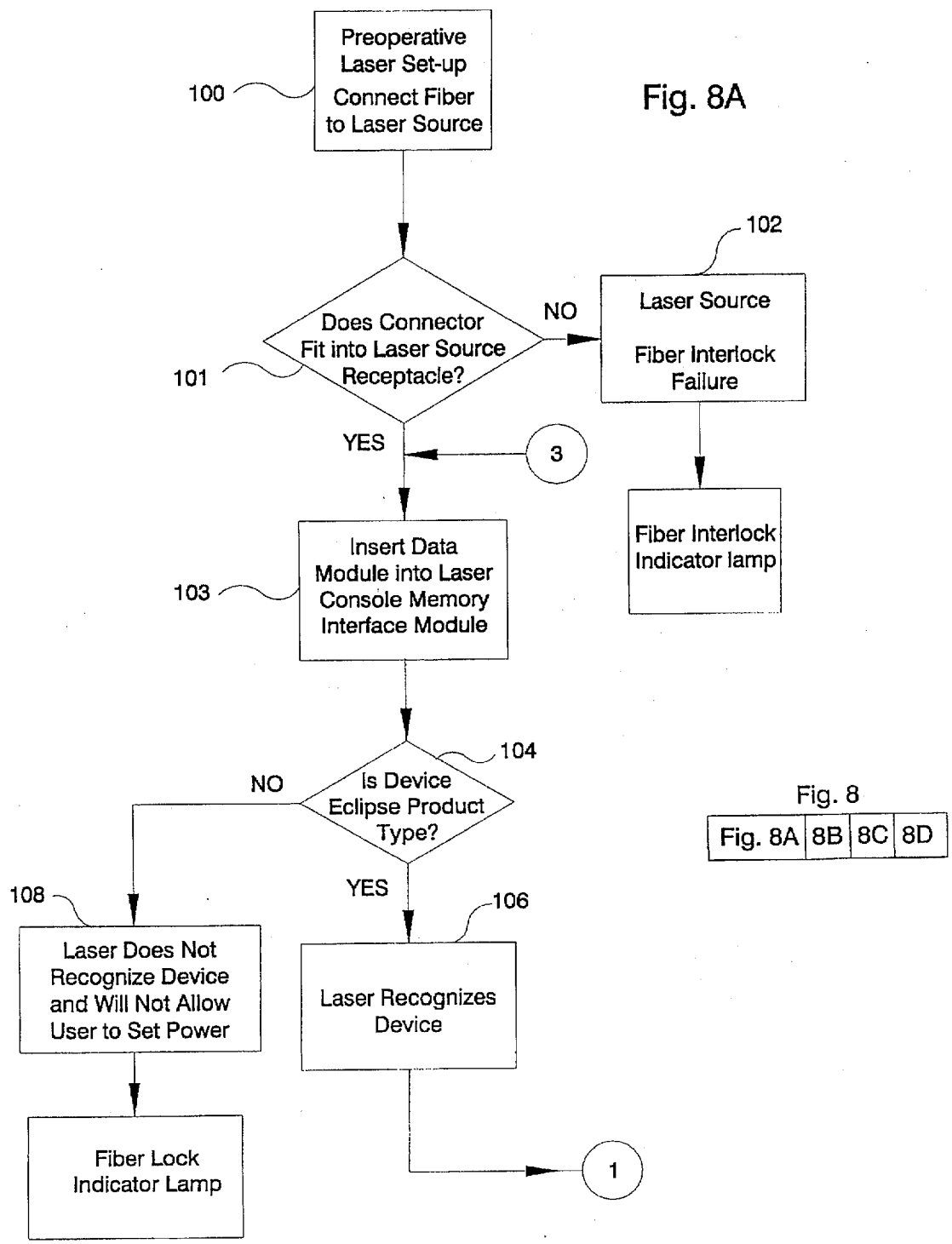

PROPRIETARY FIBER CONNECTOR AND ELECTRONIC SECURITY SYSTEM

FIELD OF THE INVENTION

This invention relates to a method and device for improving the proprietary protection, safety and procedural record-keeping capabilities of a coherent light for connection to light beam delivery equipment, such as fiber optic assemblies. More specifically, the invention relates to a specially dimensioned, proprietary laser connector and electronic security system with read/write capability which connects to a fiber optic delivery system for attachment to a laser for medical usage. The electronic security system is programmed with encrypted codes which must be detected to authorize delivery of laser energy from the laser, and the read/write capability further enables storage and retrieval of information regarding fiber optic parameters, performance and treatment parameters.

BACKGROUND OF THE INVENTION

Connectors for coupling a beam from a laser light source to a fiber optic delivery assembly designed for use in a medical procedure are known in the prior art. Fiber optic delivery assemblies for laser medical procedures generally include at least one fiber, or a bundle of silica fibers, carded within an elongated cable or jacket. A laser connector end of the fiber optic delivery assembly couples the generally disposable, medical fiber optic assembly to the laser light source. The opposite end of the fiber optic delivery assembly is configured to emit laser energy as desired, or may be configured to attach a tool for performing a desired medical procedure using laser energy. Surgical, endoscopic and interventional medical procedures performed using fiber optic delivery assemblies may include, for example, general surgery, arthroscopic laser surgery, ophthalmic surgical procedures and surgical or percutaneous cardiovascular procedures such as removal of atheromatous plaque from vessel or transmyocardial revascularization (TMR) which uses laser energy to create channels or pathways in the heart muscle.

Laser fiber optic delivery assemblies for medical uses, particularly for cardiovascular procedures such as TMR, require precise alignment between the fiber(s) of the fiber optic assembly and the laser beam emanating from the laser source. Precise alignment between the laser source and the fiber optics is necessary to enable maximal transfer of the laser beam energy to the fiber optics and to provide even distribution of laser energy throughout the fiber(s). Improper alignment and/or uneven distribution of laser energy may damage the laser connector and/or individual fibers, and may cause leakage of laser energy through the jacket. More importantly, improper alignment may result in less than optimal medical results. In addition to alignment issues, safety considerations for medical lasers generally require manufacturers to carefully design and extensively test and qualify both their lasers and the fiber optic delivery systems for connection to the lasers.

Connectors for fiber optic laser delivery assemblies must be configured to accommodate different diameters of fiber optic assemblies, and may be required to compensate for any differences between the output size of the laser beam from the source and the generally smaller diameter of the fiber optic delivery system. Lenses have been used to converge the beam from the source, as shown in U.S. Pat. No. 4,998,794, and conventional mating connectors at the source of the beam and the proximal end of the fiber optic delivery assemblies are designed to achieve an aligned coupling between the laser beam and the fiber optic assembly. Such conventional connectors may include, for example, SMA connectors having a threaded socket for attachment to a threaded receptacle at the output of the laser source. Other conventional connectors include SC connectors with push/pull latching mechanisms, generally used for fiber optic communications applications, and ST connectors with a bayonet plug and socket configuration. Conventional laser connectors generally have standardized dimensions, for example, ¼ inch internal threads, 36 threads/inch, for an SMA laser connector. Standardized dimensions permit construction specifications enabling connection of a variety of laser delivery assemblies to a laser source having such a standardized connector.

U.S. Pat. No. 4,919,508 describes a quick disconnect fiber optic coupler containing coding to determine the size of the optical fiber catheter attached thereto. A series of grooves or slots in the connecting portion of the fiber optic catheter interact with mating pins or plungers to activate micro switches and associated sensors attached to a circuit for decoding and determining the size of the fiber.

U.S. Pat. No. 5,016,964 describes an optical fiber coupler with linear input. The laser beam from the laser source is focused by one or more lenses into a focal line and the proximal end of the fiber optic assembly is arranged linearly at the focal line.

U.S. Pat. No. 4,519,390 describes a fiber optic catheter which is permanently mounted to a molded connector which attaches to a female fitting of an argon laser.

None of the above patents address the need for improving the proprietary protection, safety and record-keeping capabilities of a medical laser by providing proprietary connectors to ensure that specified, disposable, fiber optic delivery systems are attached to the medical laser and by providing an associated electronic security system with security features and having the ability to collect and store information regarding the laser treatment parameters used during particular medical procedures.

SUMMARY OF THE INVENTION WITH OBJECTS

A general object of the invention is to provide an electronic security system for a fiber optic delivery system and a proprietary connector to attach the fiber optic delivery system to a medical laser which overcomes the drawbacks and limitations of the prior art.

A more specific object of the invention is to provide an electronic security system for a fiber optic delivery system and a proprietary connector to attach the fiber optic delivery system to a medical laser wherein the dimensions of the connector are non-standard to ensure that only fiber optic delivery systems which have been pre-tested and authenticated are connected to the laser source.

Another specific object of the invention is to provide an electronic security system for a fiber optic delivery system, the security system programmed to authenticate fiber optic delivery systems and ensure such pre-tested, qualified, disposable assemblies are not reused.

One other specific object of the invention is to provide an electronic security system for a fiber optic delivery system and a proprietary connector to attach the fiber optic delivery system to a medical laser, the electronic security system having read/write capability to enable storage of laser parameters and laser treatment information.

Still another specific object of the invention is to provide an electronic security system with read/write capability for storing data regarding a fiber optic delivery system attached thereto to enable automatic laser parameter configuration when the fiber optic delivery system is attached to the medical laser.

Yet an additional specific object of the invention is to provide an electronic security system for a fiber optic delivery system having a memory interface module to interface with the medical laser source and using RF technology for encrypted communication with a data module component attached to the fiber optic delivery system, the data module component having read/write capability for storing proprietary encrypted codes and fiber optic delivery system specifications, and for writing data related to a medical procedure performed with the laser source and fiber optic delivery system.

The proprietary connector and electronic security system of the present invention includes two basic components: a non-standard connector for connecting a fiber optic delivery system to a laser source and an electronic security system for communication with the central processing unit (CPU) of the laser source. In a preferred embodiment, the console of the laser source includes a bay for mounting a component of the electronic security system and the non-standard connector.

The electronic security system includes a data module, preferably attached to the fiber optic delivery system at time of manufacture, and a memory interface module for communication with the CPU of the medical laser. The memory interface has a reader for further communication with the data module and serves as the interface between the CPU and the data module. In the preferred embodiment, the memory interface is mounted within the chassis of the laser source and communicates with the data module using RF technology.

The data module contains a conventional semiconductor chip with read/write memory which may be programmed with one or more security codes corresponding to one or more pre-tested, authenticated fiber optic delivery products. Additionally, the data module may be programmed with data specific to the fiber optic delivery system to be used and the read/write memory allows writing to the semiconductor chip of retrievable data related to the medical procedure performed with the laser source and fiber optic delivery system.

The connector fitting at the laser and the mating proprietary connector on the proximal end of the fiber optic delivery system comprises a modified laser connector having non-standard dimensions to further ensure connection of authorized, pre-tested fiber optic delivery systems to the laser.

Upon connection of the fiber optic delivery system to the laser using the proprietary connector, the security code stored in the data module is retrieved and compared with security codes stored in the CPU to ascertain whether the correct, pre-tested fiber optic delivery assembly is attached to the laser. Use of the medical laser will be disallowed unless the security code is validated. Next, the CPU receives the stored data related to the fiber optic delivery system, and such data is used to automatically or manually set laser parameters for the procedure to be performed. Information regarding the medical procedure in progress may be stored in the write memory of the electronic security system.

These and other objects, advantages and features of the present invention will become more apparent upon considering the following detailed description of preferred embodiments, presented in conjunction with the accompanying drawings.

BRIEF DESCRIPTION OF THE DRAWINGS

IN THE DRAWINGS

Figure 1:
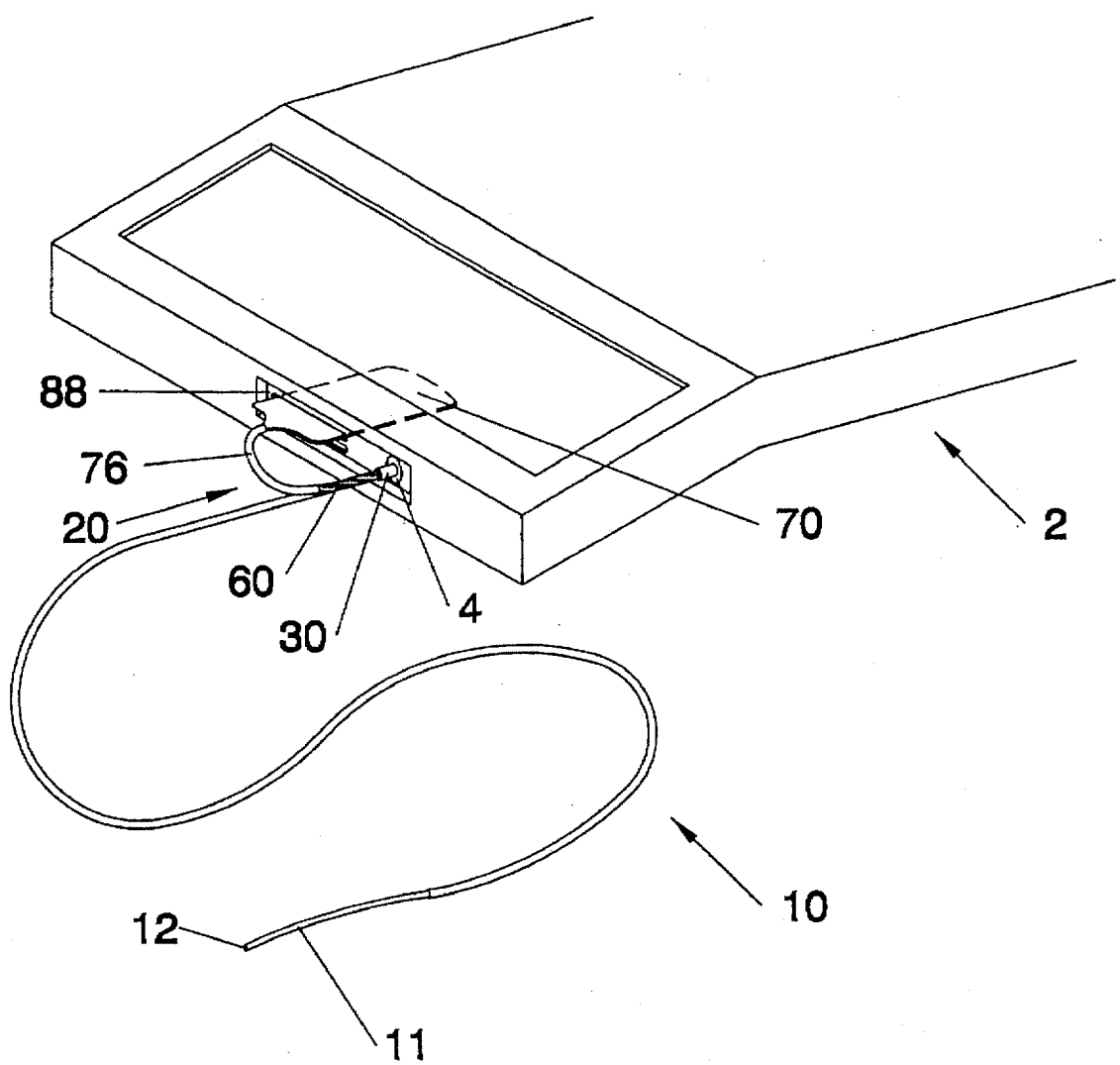

FIG. 1 is an environmental view of a portion of the top panel of a laser console showing a proprietary connector and electronic security system attached to the laser and attached to a fiber optic delivery system for use in a medical procedure.

Figures 2A, 2B:
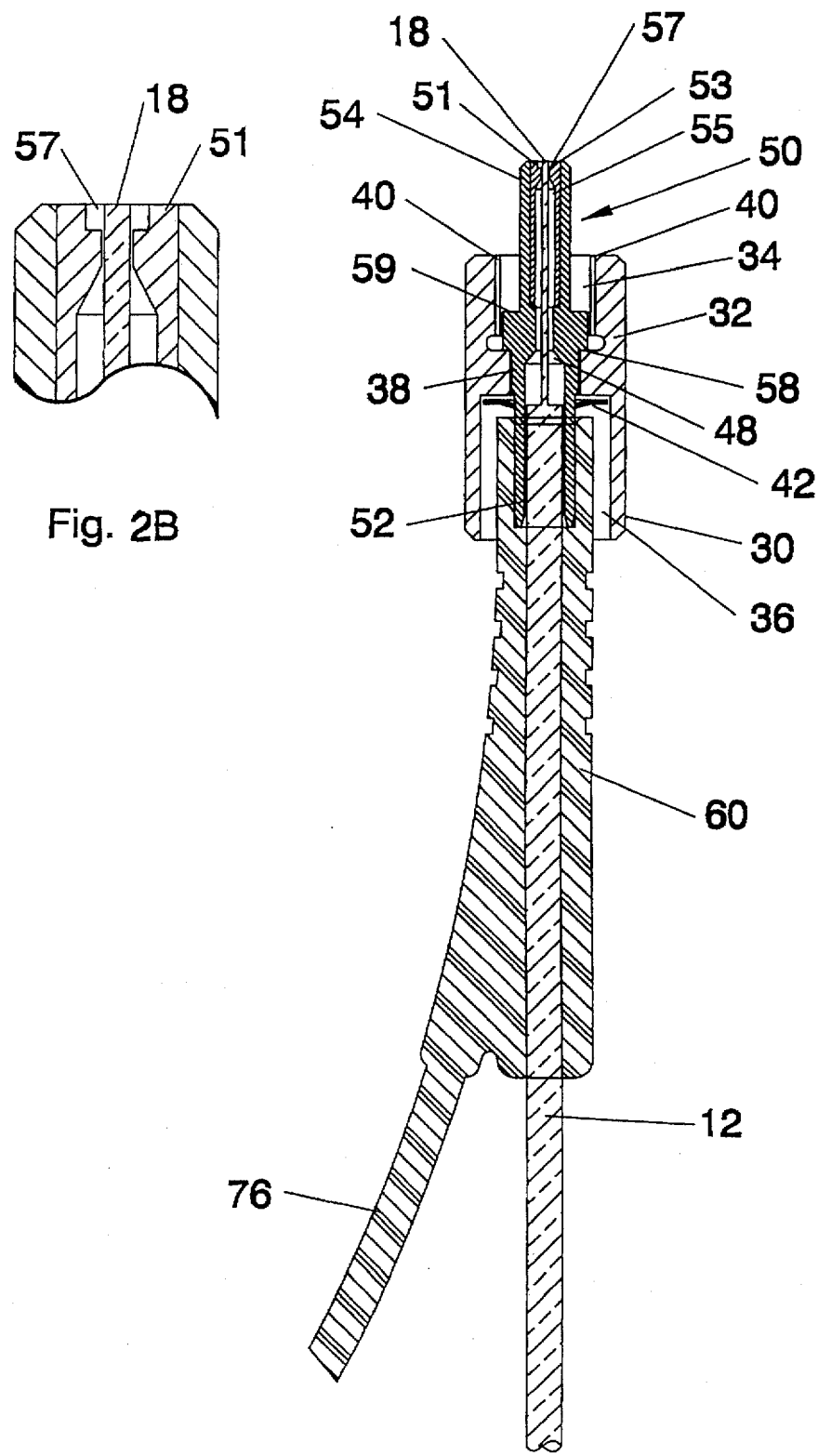

FIG. 2A is a cross sectional view of a preferred proprietary connector of the present invention shown with a fiber optic delivery system attached thereto.

FIG. 2B is an enlarged view of the proximal tip of the fiber ferrule shown in FIG. 2A.

Figure 3:
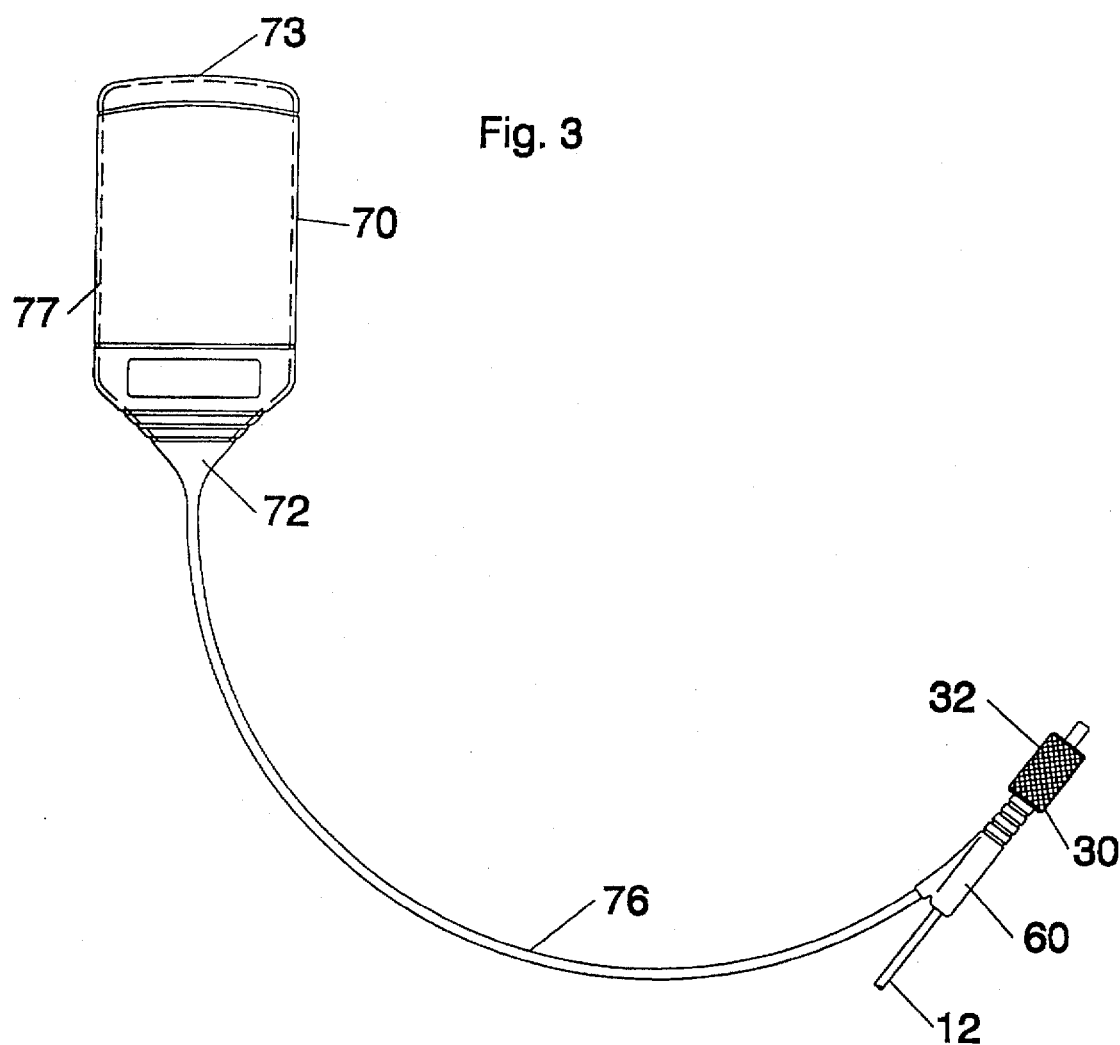

FIG. 3 is an enlarged plan view of the data module shown attached to the proprietary connector by a tether.

Figure 4A:
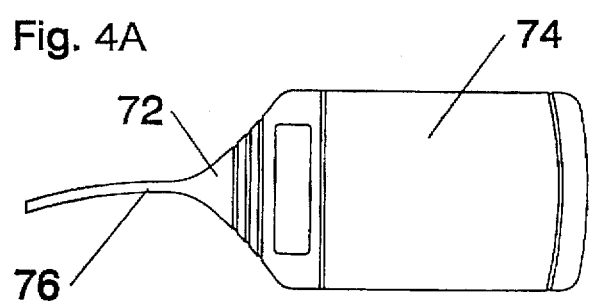

FIG. 4A is a plan view of the data module and showing the tether end attachment area.

Figure 4B:
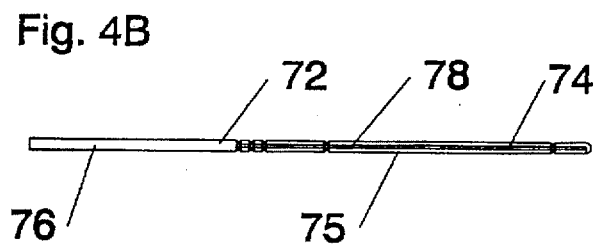

FIG. 4B is a side view of the data module of FIG. 4A.

FIG. 5A is a front view of a dual slot face plate of the memory interface for attachment within a bay of the laser chassis.

FIG. 5B is a side view of a single slot face plate showing the reader on top with an RF signal extending downwardly to the level of the slot.

FIG. 6 is a top view of the cage for insertion into the bay of the chassis for mounting the memory interface.

Figure 7:
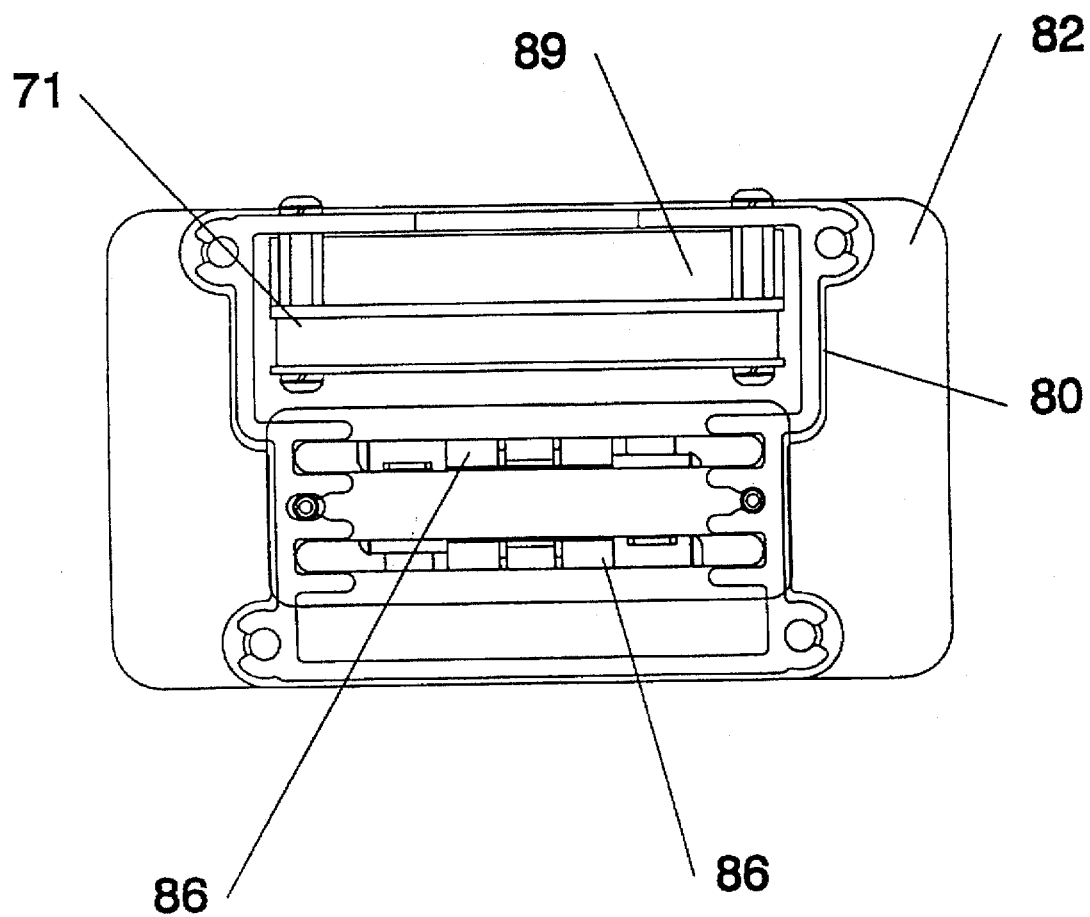

FIG. 7 is a rear view of the cage in FIG. 6 shown with the rear wall removed.

Figure 8B:
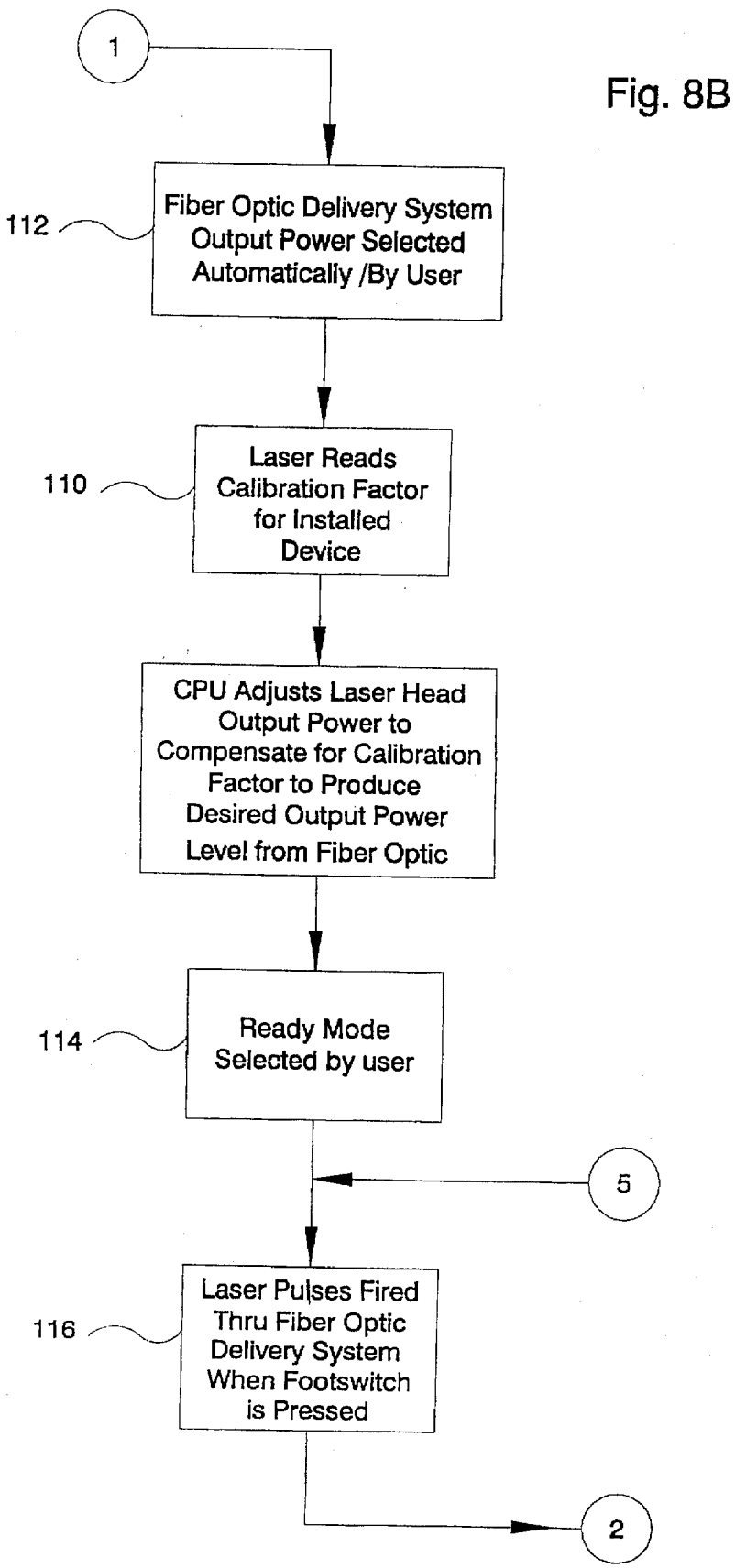
Figure 8C:
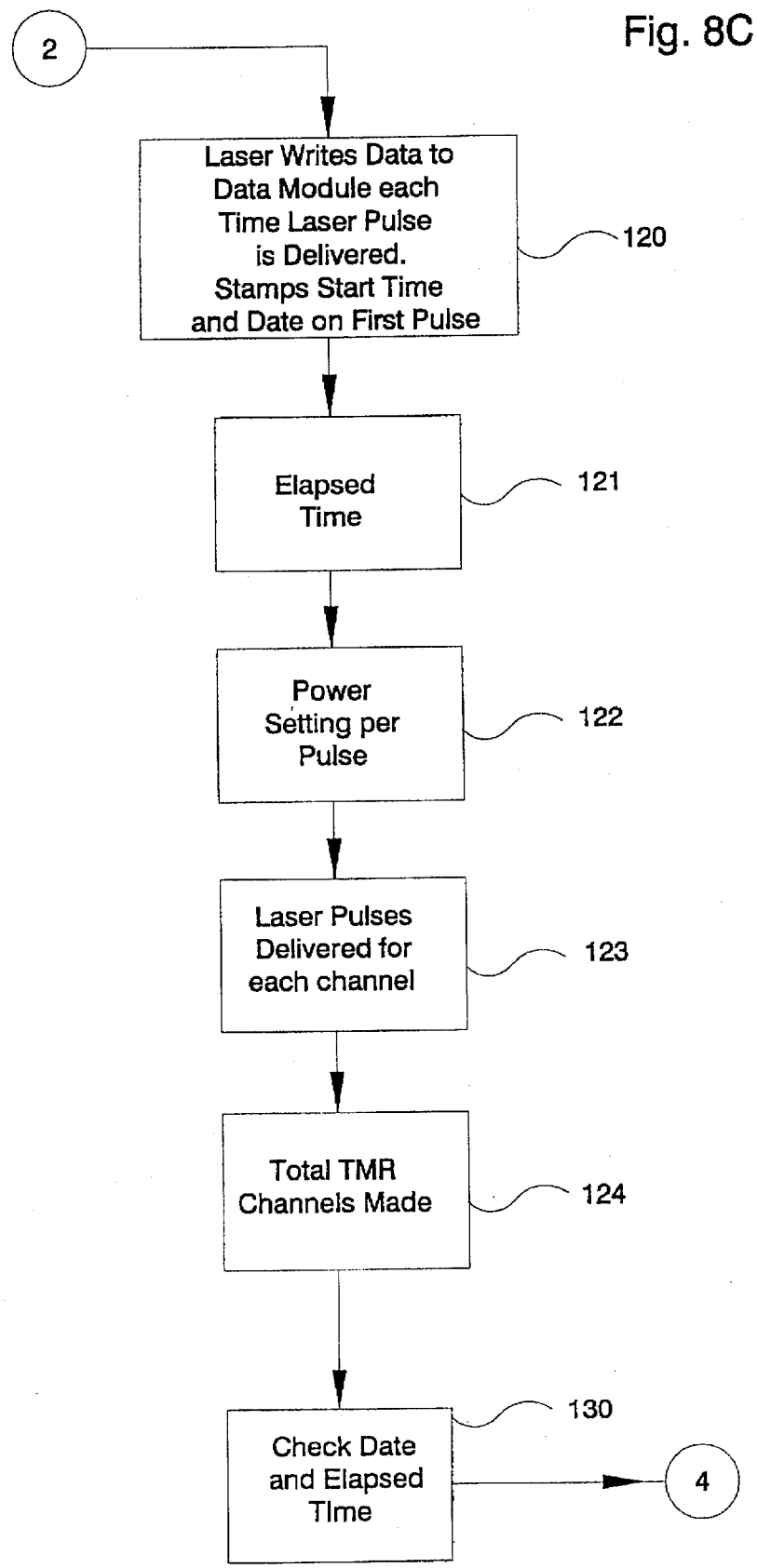
Figure 8D:
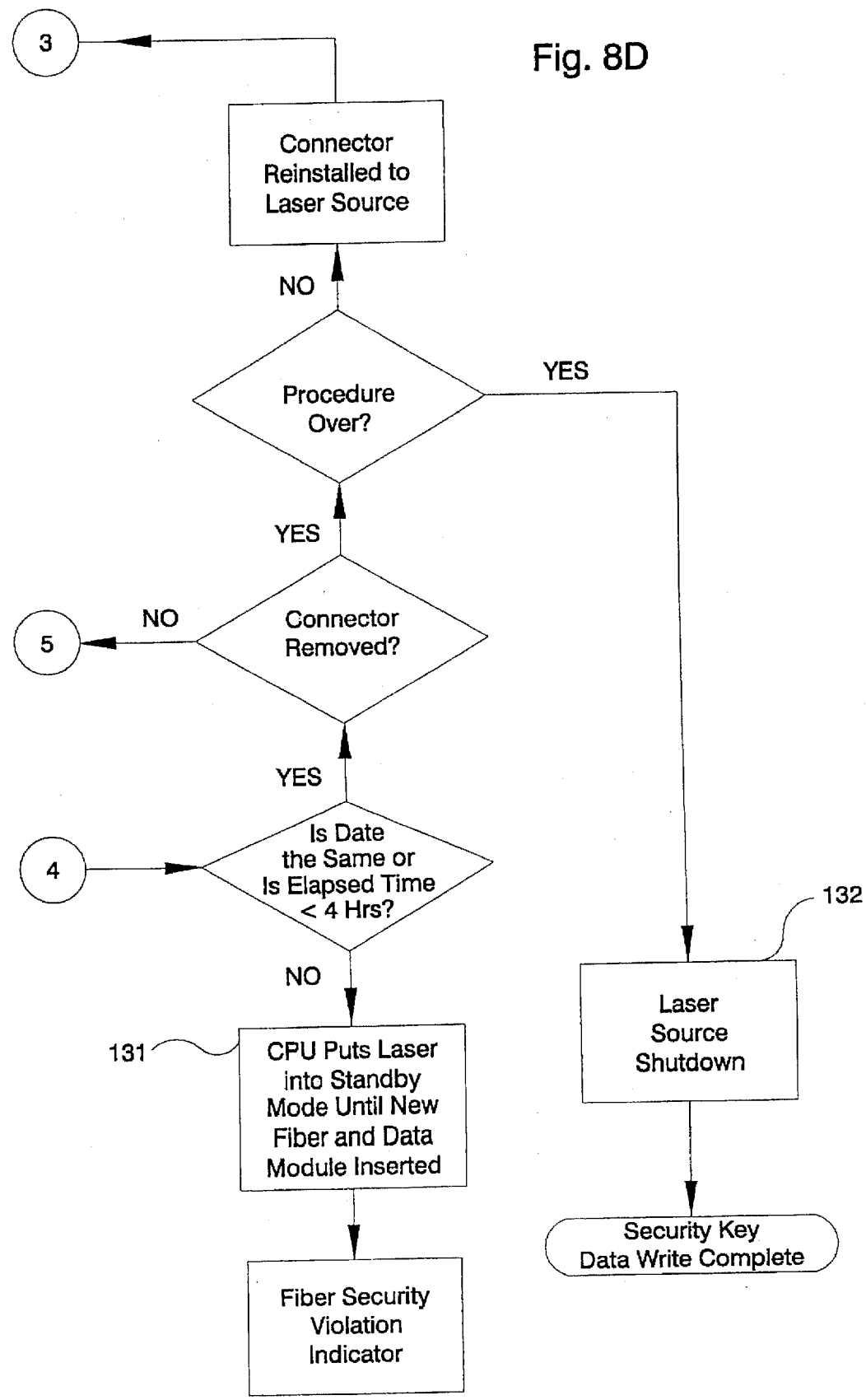

FIG. 8 consisting of FIGS. 8A, 8B, 8C and 8D is a flow chart showing operation of the proprietary connector and memory device for a medical TMR procedure.

DESCRIPTION OF PREFERRED EMBODIMENTS

A proprietary laser connector and associated electronic security system embodying principles of the present invention is shown generally in FIG. 1 as reference number 20. Referring now to FIGS. 1–3, the proprietary laser connector component of the invention, shown as reference number 30, connects to a laser source 2 and couples a fiber optic system 10 to the laser source 2. The fiber optic system 10, in the preferred embodiment, is a bundle of fiber optic fibers 11, or a single fiber, configured to perform transmyocardial revascularization (TMR) by emitting laser energy from the distal end 12 to form pathways in, at least, the myocardium of the ventricle of the heart. It will be recognized by those skilled in the art that the laser connector 30 may be configured to attach any fiber optic system to any laser for any procedure where lasers are used. It further will be recognized that the distal end 12 of the fiber optic system 10 may be otherwise configured and may attach to a tool for a laser procedure.

As shown in FIGS. 2A and 2B, the laser connector 30 is a modified SMA style of connector having a keeper nut 32 which is made from passivated stainless steel or aluminum, or other suitable metals and materials such as plastics, and suitable for sterilization and medical usage. The keeper nut 32 defines two communicating interior chambers 34, 36 which are partially separated by an interior transverse wall 38 having a generally central aperture therethrough. The keeper nut 32 defines internal 5/16 inch threads 40 surrounding interior chamber 34 for connection to mating 5/16 inch threads on the receptacle fitting (not shown) extending from the laser source. The length of the connector 30 is between approximately 0.90 inches to 1.300 inches. The length of the keeper nut is approximately 0.75 to 0.95 inches and the width is approximately 0.4 to 0.6 inches.

A unitary connector body 50 is made from stainless steel, or other suitable metals, and may be constructed as two overlapping pieces if desired. The connector body 50 defines, at the distal end, a strain relief sleeve 52 and, at the proximal end, a fiber ferrule 54. The fiber ferrule 54 is approximately 0.4640–0.4650 inches long and 0.1559–0.1561 inches in width. The connector body 50 securely mounts the fiber 12 of the fiber optic system 10 and attaches and aligns the system 10 to the laser source beam. An interior lumen 48 of the strain relief sleeve 52 houses and supports the jacketed proximal end 12 of the fiber optic system 10. A counter bore 53 at the proximal end of the fiber ferrule 54 is lined or filled with a copper insert 51 which is swaged into the counter bore 53. Tip 18 of the proximal fiber 12 is prepared in a conventional manner by polishing following removal of the jacket and buffer. The polished, uncoated tip 18 is then inserted through lumen 48, through lumen 55 of the fiber ferrule 54, and into the lumen 57 surrounded by the copper insert 51. The lumen 57 is sized approximately 5 microns larger than the diameter of the polished tip 18 and may have several sizes to accommodate specific fiber diameters. Size adjustments are made by increasing or reducing the amount of copper insert 51 and/or by changing the dimensions of the lumen 57 and/or the counter bore 53. For example, the lumen 57 may be sized 5 microns larger than 500, 550, and 940 μmicron fibers.

Following the assembly of the fiber optic system 10 to the connector body 50, the keeper nut 32 is positioned over the connector body 50 and a retaining ring 42, or C-Clip, is provided to secure the position of the connector body 50 within the keeper nut 32. An optional slot (not shown) may be provided in the keeper nut 32 to facilitate insertion of the retaining ring 42, and an optional notch (not shown) may be formed in the outer wall of the strain relief sleeve 52 for seating the retaining ring 42. For connection to the laser source 2 as shown in FIG. 1, the fiber ferrule 54 is inserted within a threaded female fitting of the laser aperture port 4 of the laser source 2, and the keeper nut 32 is secured to the threads of the female fitting by keeper nut threads 40. Tightening of the keeper nut 32 causes the nut to butt up against distal shoulder 58 of the connector body 50 thereby forcing the proximal shoulder 59 into the mating laser aperture port 4 of the laser source 2.

A flexible strain relief boot 60 is mounted over the proximal end of the fiber optic system 10 and attaches over the end of the strain relief sleeve 52. The strain relief boot 60 provides flexibility and protects the fiber optic delivery system 10 at the connector end while allowing the keeper nut 32 to swivel about the connector body 50. The strain relief boot 52 further serves as an attachment point for the data module component of the electronic security system to the fiber optic system as further described below.

Referring now to FIGS. 1, 3, and 5B, the electronic security system includes a data module component 70 and a memory interface module 71. The data module 70 is attached to the fiber optic system 10 and preferably to the laser source 2.

In a preferred embodiment, the data module 70 of the electronic security system preferably utilizes a Mifare® smart card from Mikron Graz which has an RF interface, a control unit, and RAM (read/write memory). The smart card component 77 is contained within a protective housing 73 which is attached to the strain relief boot 60 of the fiber optic system 10 by a tether 76. The tether 76 is integrally molded into the strain relief boot 60. As best shown in FIGS. 3, 4A and 4B, a tether attachment 72 extends from the tether 76 and is attached to one side of the housing 73 which generally is rectangular in shape and sized slightly larger than a credit card. The smart card 77 is enclosed within the housing 73 which preferably is formed in two planar pieces from a plastic material such as PVC. The housing 73 and the smart card component together define the data module 70. A top wall 74 and a bottom wall 75 of the housing 73 are removably secured together with the smart card, containing a Mifar PCB and ASIC chip component 78, sandwiched between. The top and bottom walls 74, 75 may be removably secured together using an adhesive, slide mounting edges/grooves 77 and/or mating geometry snap mount configurations, or a combination of adhesive and mechanical mounting geometries with the application of a heat sealing process. Preferably, the attachment is such to prevent disassembly without special tools while allowing recovery of the PCB and ASIC chip which may be re-programmed for re-use. The smart card is presented only as an example of a data module and it will be recognized by those skilled in the art that a conventional semiconductor, for example a Dallas MultiKey Semiconductor with RAM memory, Model DS 1205V, also may be used to electrically connect to the circuits of the CPU of the laser source. Any conventional semiconductor having read/write capability may be interfaced to the CPU of the laser source. The data module 70, particularly the smart card configuration, is approximately 0.08 to 0.15 inches thick and includes sufficient surface area to permit attachment of labels for procedure and patient identification data.

Referring now to FIGS. 1, 5A, 5B, and 6–7, the data module 70 is inserted into the laser source 2 when the laser connector 30 is attached to the laser aperture port 4. A bay in the console of the laser module 2 is used to insert a cage, or housing 80, which is conventionally mounted to bay. The housing 80 is similar to a floppy-drive mounting unit and defines a frame 82 with a back wall 84. The frame preferably is constructed from extruded aluminum and sheet metal to minimize RF emissions. The frame defines one or more ports 86 in a front bezel plate 88 for insertion of one or more data module cards 70 which may or may not be attached to different fiber optic delivery systems. Conventional detents are provided to enable the operator to detect when the data module 70 is fully inserted. As best shown in FIGS. 5B and 7, the memory interface module 71, including a read/write component of the electronic security system, is mounted above the data module ports 86 in a closed bay 89. A micro switch (not shown), or a beam type sensor, is positioned to detect when a data module card 70 is fully inserted in a port 86 thereby verifying correct placement of the data module 70. The bezel 86 may be configured as in FIG. 5A, or preferably as in FIG. 1 to include the laser aperture port 4. The memory interface module 71 is connected to the CPU by, for example, an electrical connection, an optical pathway or a wireless, radio-frequency (RF) link. In the preferred embodiment, the memory interface module 71 is electrically connected to the CPU.

Following insertion of a data module card 70 into a port 86 and connection of the proprietary laser connector 30, the electronic security system is utilized to access data stored in the data module 70. The EEPROM memory in the ASIC chip may be programmed to store a wide variety of data, for example, a security code corresponding to one, pre-tested authenticated fiber optic delivery system product, lot number and date of manufacture, or data sufficient to enable determination of fiber type when read, such data being shown in Table A below. Programming of the security code is accomplished using conventional encryption data storage, and communication between the interface and the CPU is established using a software communication program to establish serial or parallel port communications.

Table A shows a Storage Table in the memory of the data module 70 programmed with a stored security code, such as a password or serial number, which is encrypted using an encryption algorithm. A number of such codes may be stored to enable continued use of the semiconductor without reprogramming in the event that a particular code becomes known. In addition to storage of security codes, the Storage Table of the data module 70 also contains the stored Product Type information discussed above which allows the device to ascertain information about the type of proprietary delivery system present. A Laser Calibration Factor also is stored within the storage table.

TABLE A

| Storage Table DATA ENCODED |
| --- |
| Security Code |
| Product Type |
| Laser Calibration Factors |

Referring now to Table B below, the data module 70 also includes a Write Table to enable storage of information accumulated during the medical procedure to be performed. In the case of TMR procedures using pulsed lasers, the Write Table includes storage of, for instance, accumulated information regarding the time and date the fiber device is first used, number of pulses and the power level used for each pulse, the total number of pulses delivered, and the total number of TMR channels created.

TABLE B

| Write Table DATA STORED |
| --- |
| Time/Date |
| Power Level/No. of Pulses |
| Total No. of Pulses |
| Total No. of TMR Channels |
| Master Key |

For service purposes, a stand alone Master Key card (not shown) allows any compatible fiber to be attached to the laser source for testing purposes. The laser source writes the number of uses of the Master Key card to limit the number of uses prior to reconditioning thereby preventing misuse of such Keys. The Master Key also includes a service engineer identification number.

Referring now to FIG. 8, consisting of FIGS. 8A, 8B, 8C and 8D, a flow chart shows a typical use of the proprietary connector 30 and electronic security system of the present invention for a TMR procedure. The procedure is presented as an example only and it will be recognized by those skilled in the art that the information encoded and the information stored by the electronic security system may vary according to the particular application for the laser.

At step 100, an attempt is made to connect a fiber to the laser aperture port 4, and the proprietary dimensions of the connector 30 help to ensure that only correct fiber optic assemblies with like sized connector ends are attached to the laser source as shown in steps 101, 102. A failure to interlock may be shown on a fiber interlock indicator lamp.

Upon attachment of a correctly sized connector end of a proprietary, unused fiber optic system to the laser source 2, and insertion of the data module card 70 into the laser console at step 103, RF communication is established between the data module 70 and the memory interface 71, and between the memory interface 71 and the CPU of the laser console. The CPU senses connection of the fiber optic delivery system and commands the memory interface module to communicate with the data module for retrieval of the encrypted data. The CPU determines whether the fiber optic system is an authorized system at step 104 by comparing the stored code with the proprietary code retrieved by the memory interface module and representative of the attached fiber optic system. The CPU further determines whether all parameters are in valid ranges. Full access to the laser source is allowed at step 106 if the codes are successfully compared, thereby testing whether an authorized, pre-tested fiber is attached to the laser, or access is denied at step 108. The validation procedure further ensures that the particular fiber optic delivery system has not been used previously thereby ensuring one time use of laser delivery systems.

The memory interface next reads the stored data in the data module and transmits to the CPU at step 110 transmission performance data specific to the connected fiber optic delivery system, such as the appropriate Calibration Factor. Upon receiving the transmission performance date, the CPU automatically sets the laser head power level of the laser head at 112 to cause the fiber output power of the particular product to be equal to a predetermined clinical power setting on the laser. Alternatively, the user manually may set the power level at step 112. Initial enabling of the laser source for activation occurs at step 114 following automatic or user selection of the output power of the fiber optic delivery system at step 112.

Upon activation of the calibrated laser beam at 116, the Time/Date feature in the Write Table is activated at 120 and the Date of the procedure is written into the Write Table along with the time of laser activation. Simultaneously, data begins to be written to the data module upon each pulse of the laser. The electronic security system is programmed to allow laser access for a particular period of time, for example, four hours, to ensure, in the case of a TMR procedure, optimal channel formation and to allow multiple removal and re-insertion of the fiber during one TMR procedure.

Start and stop times for the TMR procedure are stored in the Write Table at step 121, thereby allowing computation of the elapsed time of the procedure, and accumulated information regarding the channels formed is also stored. For instance, the electronic security system may be programmed to recognize that a particular burst of pulses is required to create a single channel. In this case, the Write Table would accumulate information about each pulse power level at step 122, the total delivered pulses at step 123, and the total number of channels created at step 124. Additionally, the stored information may include data showing use of ancillary medical equipment during the medical procedure performed.

As the TMR procedure continues, the fiber optic system 10 may be removed when desired prior to expiration of the preprogrammed time limit. Following expiration of the time limit, step 130, the CPU will automatically terminate the laser procedure at step 131.

The stored information may be accessed by a reader designed to retrieve the information for purposes such as maintenance of patient medical records, clinical research, statistical analysis and the like. Retrieval of data is accomplished by inserting the data module into a separate data retrieval reader (not shown) to extract and print out the stored data. Identification of the data module is assured by manually writing the patient's name, hospital identification, and other relevant information on a label attached to the data module.

While this invention has been described in connection with preferred embodiments thereof, given the teachings herein, modifications and changes may be made by those skilled in the art to which it pertains without departing from the spirit and scope of the invention. For instance, the proprietary connector may be a modification of any standard fiber optic connection. Accordingly, the aspects discussed herein are for illustration only and should not limit the scope of the invention herein which is defined by the claims.

What is claimed is:

1. A proprietary connector and electronic security system for coupling only proprietary electromagnetic (EM) energy medical delivery device for a medical procedure to a EM energy source comprising:
   a) the medical EM energy delivery device adapted to be coupled to the medical EM energy delivery device having a central processing unit (CPU),
   b) a connector adapted for attaching a proximal end of one of the only proprietary EM energy delivery device to the EM energy source, and
   c) electronic memory means for storing data of at least one security code and data corresponding to usage of the connector, the memory means is attached and juxtaposed to the connector and is adapted for communication with the CPU,
   whereby input of the data of at least one security code and data corresponding to usage of the connector causes the CPU to enable the EM energy source thereby ensuring reliable and safe use of the medical EM energy delivery device.

2. The proprietary connector and electronic security system of claim 1 wherein the connector is a fiber optic connector, the proprietary medical EM energy delivery device is a fiber optic delivery device, and the EM energy source is a laser, the fiber optic connector comprising:
   a connector body having a length of approximately 1.2 inches, the connector body defining a fiber ferrule end and a strain relief end, the fiber ferrule end being approximately 0.46 inches long and 0.16 inches in diameter, the strain relief end being approximately 0.70 inches in length; and
   keeper nut means adapted for attaching to the connector body and to the laser, the keeper nut means being approximately 0.9 inches long, 0.5 inches wide, and having approximately 40, 5/16 inch internal threads.

3. The proprietary connector and electronic security system of claim 2 wherein the fiber ferrule end further comprises a lumen surrounded by a counter bored well having a copper insert, the lumen sized to define a width substantially 5 microns larger than a diameter of a proximal end of a fiber of the fiber optic delivery device.

4. The method of claim 3 further including the step of storing data during a transmyocardial revascularization (TMR) procedure wherein the electronic memory means stores data of at least one calibration factor, a date of the TMR procedure, a start time of the TMR procedure, a record of a first connection of the laser to the optical fiber, a number of pulses and energy emitted per formed channel and number of channels formed.

5. The proprietary connector and electronic security system of claim 2 wherein the connector body is of unitary construction.

6. The proprietary connector and electronic security system of claim 2 further comprising retainer means for securing the connector body within the keeper nut means when the keeper nut means is attached to the laser by the internal threads.

7. The proprietary connector and electronic security system of claim 2 further comprising a strain relief means for attachment over the strain relief end.

8. The proprietary connector and electronic security system of claim 7 wherein the strain relief means comprises at least two sleeves, a first sleeve for attachment over the strain relief end and a second sleeve for attaching the electronic memory means to the fiber optic connector.

9. The proprietary connector and electronic security system of claim 8 wherein the second sleeve attaches a tether means extending to the electronic memory means.

10. The proprietary connector and electronic security system of claim 1 wherein the electronic memory means comprises at least one interface and at least one data module, the at least one interface establishing communication between the data module and the CPU, the data module having memory for storage of at least one security code and storage of data accumulated during the medical procedure.

11. The proprietary connector and electronic security system of claim 10 wherein the data module comprises at least one read/write semiconductor device.

12. The proprietary connector and electronic security system of claim 10 wherein the data module is a smart card.

13. The proprietary connector and electronic security system of claim 12 wherein the smart card stores data of product type, serial number, calibration factor, date of use, elapsed laser procedure time, number of performed medical procedures, laser operating parameters during the medical procedure, number and power level of laser pulses transmitted.

14. The proprietary connector and electronic security system of claim 10 wherein the memory comprises at least one storage table for storing the at least one security code and at least one calibration factor, and at least one table for writing the data accumulated during the medical procedure.

15. The proprietary connector and electronic security system of claim 14 wherein the at least one calibration factor is a power setting for the EM energy source, and the data in the writing table is at least a date and a start time of the procedure and record of first use of the proprietary EM energy delivery device.

16. The proprietary connector and electronic security system of claim 14 wherein the medical procedure is transmyocardial revascularization, the laser is a pulsed laser, and the data in the table for writing additionally is at least a total number of pulses delivered and a total number of channels created during the transmyocardial revascularization procedure.

17. The proprietary connector and electronic security system of claim 16 wherein the CPU comprises means for recognizing and comparing a plurality of encrypted codes; means for automatically calibrating the laser in response to downloading of a calibration factor from the electronic memory means; means for determining a total number of laser pulses delivered per channel; means for storing power settings for each of the total number of laser pulses delivered; means for determining a total number of laser channels created in a transmyocardial revascularization procedure, and clock means.

18. The proprietary connector and electronic security system of claim 17 wherein the means for recognizing means for automatically calibrating, means for determining a total number of laser pulses delivered per channel, means for storing power settings, and means for determining a total number of laser channels created is programming for the CPU.

19. The proprietary connector and electronic security system of claim 10 wherein the at least one security code is at least one encrypted code programmed into the data module and the CPU, the CPU includes means for comparing the at least one security code and usage data prior to enabling the EM energy source.

20. The method of claim 11 further including the step of storing data during a medical procedure in the electronic memory means, the data contains at least one calibration factor, a date of the medical procedure, a start time of the medical procedure, a record of a first connection of the EM energy source to the medical EM energy delivery device.

21. The method of claim 1 wherein the EM energy source is a laser and the EM energy delivery device is an optical fiber.

22. A proprietary connector and security system for coupling only a proprietary medical fiber optic laser delivery device for a laser source comprising:

the medical fiber optic laser delivery device adapted to be connected to the laser source;

electronic memory means attached to the fiber optic delivery device and adapted to communicate with a central processing unit (CPU) that controls the laser source, the electronic memory means comprising at least one interface and at least one data module, the at least one interface adapted for establishing communication between the data module and the CPU, the data module having mad/write memory for storage of at least one security code and data corresponding to usage of the proprietary connector, and storage of data accumulated during the medical procedure;

a connector body having a length of approximately 1.2 inches, the connector body defining a fiber ferrule end and a strain relief end; the fiber ferrule end adapted for attachment to a fitting of the laser source and being approximately 0.46 inches long, 0.16 inches in diameter, and defining a lumen having a diameter of approximately 0.062 inches; the strain relief end adapted for attachment of the specific fiber optic laser delivery device and being approximately 0.70 inches in length and defining a lumen having a diameter of approximately 0.125 inches;

keeper nut means for attachment to the connector body and adapted for attachment to the fitting of the laser source, the keeper nut means being approximately 0.9 inches long, 0.5 inches wide, and having approximately 40, 5/16 inch internal threads; and retainer means for attachment over the connector body for securing the connector body within the keeper nut means;

whereby the laser source is enabled when the CPU processes and in accordance with the at least one security code and acceptable data corresponding to usage of the proprietary connector, thereby ensuring reliable and safe use of the medical fiber optic laser delivery device.

23. The proprietary connector and electronic security device of claim 22 wherein the medical procedure is transmyocardial revascularization, the laser is a pulsed laser, the data module is a smart card with data related to product type and serial number, and the read/write memory comprises at least one storage table for storing the at least one security code and at least one calibration factor, the read/write memory further, having at least one table for writing at least a date of the procedure, a start time of the procedure, a record of a first connection of the fiber optic delivery device to the laser and a number of pulses and energy emitted per formed channel, number of channels created.

24. A method of ensuring reliable and safe use of a proprietary medical electromagnetic (EM) energy delivery device for a medical procedure with discrete components requiring connection comprising the steps of:

a) providing a connector with an electronic security system for coupling only the proprietary medical EM energy delivery device to a EM energy source, wherein the EM energy source is adapted to be coupled to the medical EM energy delivery device and has a central processing unit (CPU), the connector is adaptable for attachment of a proximal end of the EM energy delivery device to the source of EM energy, and an electronic memory means for storing at least one security code and data corresponding to usage of the connector, the memory means forms part of the proprietary connector which communicates with the CPU;

b) connecting the EM energy source to the medical EM energy delivery device; and c) processing the at least one security code and the data corresponding to usage of the EM energy delivery device stored in the electronic memory means by the CPU; and d) enabling the EM energy source by the CPU when the at least one security code and acceptable data corresponding to usage of the connector are in accordance with required data.

* * * * *